United States Patent
Chandra et al.

(10) Patent No.: US 9,358,186 B2
(45) Date of Patent: Jun. 7, 2016

(54) FOAMED PERSONAL CARE COMPOSITION OBTAINABLE BY AERATING AND HEATING A BASE COMPOSITION

(71) Applicant: Conopco, Inc., Englewood Cliffs, NJ (US)

(72) Inventors: Lalitesh Chandra, Great Sutton (GB); Gareth James Perriam, Prescot (GB); Jordan Todorov Petkov, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/353,958

(22) PCT Filed: Oct. 15, 2012

(86) PCT No.: PCT/EP2012/070390
§ 371 (c)(1),
(2) Date: Jun. 20, 2014

(87) PCT Pub. No.: WO2013/060590
PCT Pub. Date: May 2, 2013

(65) Prior Publication Data
US 2014/0350224 A1   Nov. 27, 2014

(30) Foreign Application Priority Data
Oct. 25, 2011 (EP) .................... 11186438

(51) Int. Cl.
*A61K 8/04*  (2006.01)
*A61K 8/64*  (2006.01)
*A61Q 5/12*  (2006.01)
*A61Q 19/00*  (2006.01)

(52) U.S. Cl.
CPC ............. *A61K 8/046* (2013.01); *A61K 8/645* (2013.01); *A61Q 5/12* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 2001/0033826 A1 | 10/2001 | Roulier | |
| 2012/0213725 A1* | 8/2012 | Galleguillos | A61K 8/463 424/70.16 |

FOREIGN PATENT DOCUMENTS

| | | | | |
|---|---|---|---|---|
| CH | 674804 A | 7/1990 | | |
| CL | CH674804 | 7/1990 | | |
| EP | 1520575 A1 * | 4/2005 | ............ | A61K 8/39 |
| EP | 2042154 A1 | 4/2009 | | |
| EP | 1046387 | 5/2015 | | |
| WO | WO0222771 A1 | 3/2002 | | |
| WO | WO 0222771 A1 * | 3/2002 | | |
| WO | WO03094874 | 11/2003 | | |

OTHER PUBLICATIONS

PCT International Search Report in PCT application PCT/EP2012/070390 dated Sep. 6, 2013 with Written Opinion.
IPRP2 in PCTEP2012070390 dated Apr. 7, 2014, WO.

* cited by examiner

*Primary Examiner* — Robert A Wax
*Assistant Examiner* — Melissa Mercier
(74) *Attorney, Agent, or Firm* — Karen E. Klumas

(57) ABSTRACT

Foamed personal care composition obtainable by aerating a base composition and heating at from 30 to 100° C. for from 10 minutes to 100 hours. The composition comprises a proteinaceous material and is suitable for use in care of the hair.

6 Claims, No Drawings

FOAMED PERSONAL CARE COMPOSITION OBTAINABLE BY AERATING AND HEATING A BASE COMPOSITION

The present invention relates to an improved foamed personal care composition.

Despite the prior art there remains a need for improved aerated compositions.

Accordingly, the present invention provides a foamed personal care composition obtainable by aerating a base composition and heating at from 30 to 100° C. for from 10 minutes to 100 hours.

Preferably, the composition is obtainable by heating at from 36 to 75° C.

Preferably, the composition is obtainable by heating at from 45 to 55° C.

Preferably, the composition is obtainable by heating at from 30 to 100° C. for from 20 min to 90 min.

We have surprisingly found that heating the formulation after aerating provides a composition with significantly improved sensory characteristics.

Preferably, the composition comprises a proteinaceous material.

Preferably, the proteinaceous material is a hydrolysed proteinaceous material.

Preferably, wherein the proteinaceous material is hydrolysed vegetable protein.

Preferably, the proteinaceous material is Keravis® commercially available from Croda.

The proteinaceous component provides further enhanced sensory characteristics for the consumer.

The compositions of the invention are foamed with air or inert gas up to a degree of foam-up which typically is at least 5% of air or inert gas at 20° C., preferably 10 percent and up to 100 percent, more preferably between 15 and 70 percent and particularly between 20 and 60% by volume. It is preferred that from least 40% by volume of the product is foamed.

The compositions may be foamed with an inert gas or air, preferably they are foamed with air.

Preferably the aerated compositions comprise substantially no hydrocarbon based propellant. Preferably, the compositions of the invention comprise from 0 to 5% wt. and more preferably from 0 to 2% wt. hydrocarbon based propellant.

In the context of the present invention the definition of a stable foam is a product characterized in that it has homogeneously distributed a gaseous substance in the form of small gas bubbles which remain in this homogeneous distribution over a period of at least one week, preferably at least one month and particularly at least 6 months or longer if stored at room temperature 20° C.

Preferably, the average bubble size on initial manufacture is from 1 microns in diameter to 200 microns, preferably from 6 microns to 50 microns. It is preferable that the average bubble size is no more than 50 times its initial diameter, preferably no more than 40 times its original diameter after storage at 45° C. for 28 days. Preferably the average bubble size after 4 months storage at 45° is 500 microns or less, more preferably 300 microns or less.

Bubble size is based on the number average diameter.

The diameters are measured using an Olympus microscope, camera and associated AnalySIS® software.

In the context of the present invention an aerated composition does not comprise a product that is dispersed from an aerosol, or a consumer operated container comprising a valve. The aerated composition of the present invention is stored in a container and applied to the hair of the consumer by scooping sufficient product with the fingers and directly applying to the hair.

Preferably, the composition comprises a cationic surfactant for conditioning the hair. Suitable cationic conditioning surfactants can be used singly or in admixture.

Preferably the cationic conditioning surfactant is a quaternary ammonium or an amine having at least one long chain alkyl group that has on average around about 16 to about 40 carbon atoms.

Suitable cationic surfactants for use in hair conditioners of the invention include cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, and the corresponding hydroxides thereof. Further suitable cationic surfactants include those materials having the CTFA designations Quaternium-5, Quaternium-31 and Quaternium-18. Mixtures of any of the foregoing materials may also be suitable.

Preferably the cationic surfactant is insoluble. Insoluble in this context is defined as materials which at 20° C. do not form isotropic, clear solutions in water at greater than 0.2 Wt %.

Preferred cationic surfactants are moncationic, more preferred surfactants include the compounds distearyldimethylammonium, dicetyldimethylammonium, tricetylmethylammonium,-behenyltrimethylammonium, stearyl benzyl dimethylammonium, suitable amines include distearylamine, distearylmethylamine, behenylamine, behenylmethylamine, behenyldimethylamine, dicetylamine, dicetylmethylamine, tricetylamine.

Preferably the cationic salt is a combination of behenyltrimethylammonium/salt with a second cationic conditioning surfactant. In the most preferred form the cationic conditioning surfactant is behenyltrimethylammonium salt, in particular the chloride. In compositions of the invention, the level of cationic surfactant is preferably from 0.1 to 10%, more preferably 0.5 to 7%, most preferably 1 to 5% by weight of the total composition.

Compositions of the invention preferably incorporate a fatty material, preferred fatty material are fatty alcohol and fatty acid, fatty alcohol is especially preferred The combined use of fatty alcohol materials and cationic surfactants in conditioning compositions is believed to be especially advantageous, because this leads to the formation of a lamellar phase, in which the cationic surfactant is dispersed.

Preferred fatty alcohols comprise from 8 to 22 carbon atoms, more preferably 16 to 20. Examples of suitable fatty alcohols include cetyl alcohol, stearyl alcohol and mixtures thereof. The use of these materials is also advantageous in that they contribute to the overall conditioning properties of compositions of the invention.

The level of fatty alcohol material in conditioners of the invention is conveniently from 0.01 to 10%, preferably from 0.1 to 5% by weight of the composition. The weight ratio of cationic surfactant to fatty alcohol is suitably from 10:1 to 1:10, preferably from 4:1 to 1:8, optimally from 1:1 to 1:4.

Compositions of the invention may comprise silicones, in particular silicone emulsions.

Suitable silicone emulsions include those formed from silicones such as polydiorganosiloxanes, in particular polydimethylsiloxanes which have the CTFA designation dimethicone, polydimethyl siloxanes having hydroxyl end groups which have the CTFA designation dimethiconol, and aminofunctional polydimethyl siloxanes which have the CTFA designation amodimethicone.

The emulsion droplets may typically have a Sauter mean droplet diameter ($D_{3,2}$) in the composition of the invention ranging from 0.01 to 20 micrometer, more preferably from 0.2 to 10 micrometer.

A suitable method for measuring the Sauter mean droplet diameter ($D_{3,2}$) is by laser light scattering using an instrument such as a Malvern Mastersizer.

Suitable silicone emulsions for use in compositions of the invention are available from suppliers of silicones such as Dow Corning and GE Silicones. The use of such pre-formed silicone emulsions is preferred for ease of processing and control of silicone particle size. Such pre-formed silicone emulsions will typically additionally comprise a suitable emulsifier such as an anionic or nonionic emulsifier, or mixture thereof, and may be prepared by a chemical emulsification process such as emulsion polymerisation, or by mechanical emulsification using a high shear mixer. Pre-formed silicone emulsions having a Sauter mean droplet diameter ($D_{3,2}$) of less than 0.15 micrometers are generally termed microemulsions.

Examples of suitable pre-formed silicone emulsions include emulsions DC2-1766, DC2-1784, DC-1785, DC-1786, DC-1788 and microemulsions DC2-1865 and DC2-1870, all available from Dow Corning. These are all emulsions/microemulsions of dimethiconol. Also suitable are amodimethicone emulsions such as DC939 (from Dow Corning) and SME253 (from GE Silicones).

Also suitable are silicone emulsions in which certain types of surface active block copolymers of a high molecular weight have been blended with the silicone emulsion droplets, as described for example in WO03/094874. In such materials, the silicone emulsion droplets are preferably formed from polydiorganosiloxanes such as those described above. One preferred form of the surface active block copolymer is according to the following formula:

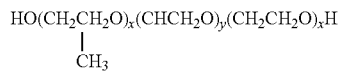

wherein the mean value of x is 4 or more and the mean value of y is 25 or more.

Another preferred form of the surface active block copolymer is according to the following formula:

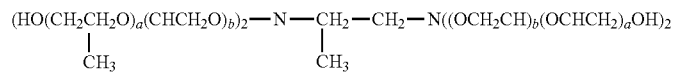

wherein the mean value of a is 2 or more and the mean value of b is 6 or more.

Mixtures of any of the above described silicone emulsions may also be used.

Silicone will generally be present in a composition of the invention at levels of from 0.05 to 10%, preferably 0.05 to 5%, more preferably from 0.5 to 2% by total weight of silicone based on the total weight of the composition.

Other ingredients may include viscosity modifiers, preservatives, silicones, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, compositions of this invention also contain adjuvants suitable for hair care. Generally such ingredients are included individually at a level of up to 2%, preferably up to 1%, by weight of the total composition.

Among suitable hair care adjuvants, are:

(i) natural hair root nutrients, such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts.

(ii) hair fibre benefit agents. Examples are:

ceramides, for moisturising the fibre and maintaining cuticle integrity. Ceramides are available by extraction from natural sources, or as synthetic ceramides and pseudoceramides. A preferred ceramide is Ceramide II, ex Quest. Mixtures of ceramides may also be suitable, such as Ceramides LS, ex Laboratoires Serobiologiques.

free fatty acids, for cuticle repair and damage prevention. Examples are branched chain fatty acids such as 18-methyleicosanoic acid and other homologues of this series, straight chain fatty acids such as stearic, myristic and palmitic acids, and unsaturated fatty acids such as oleic acid, linoleic acid, linolenic acid and arachidonic acid. A preferred fatty acid is oleic acid. The fatty acids may be added singly, as mixtures, or in the form of blends derived from extracts of, e.g. lanolin.

Mixtures of any of the above active ingredients may also be used.

The composition of the invention comprises a lamellar structure. It is preferred if the composition does not have a micellar structure.

Preferably, the composition is an aerated product in that it is packaged in an aerated form.

The compositions of the invention are primarily intended for topical application to the body, preferably the hair and/or scalp of a human subject in rinse-off or leave-on compositions.

The compositions provided by the invention may be aqueous conditioner compositions, used by massaging them into the hair followed by rinsing with clean water prior to drying the hair.

The invention will be further described by way of the following non-limiting examples.

EXAMPLE 1

A souffle formulation according to the invention.

| Ingredient | % Wt. |
|---|---|
| Stearamidopropyl dimethylamine | 1.35 |
| Cetearyl alcohol | 6 |
| Behentrimmonium chloride | 0.49 |
| PEG-150 distearate | 0.02 |
| Water and hydrolysed vegetable protein PG-propyl silanetriol | 0.2 |
| Cyclopentasiloxane, trimethylsiloxysilicate and dimethiconol | 0.4 |
| Dimethicone and trideceth-5 | 0.6 |
| Lactic acid | 0.37 |
| EDTA | 0.1 |
| Preservative | 0.37 |
| Fragrance | 0.25 |
| Water | To 100 |

Aeration Protocol

1 Kg of unaerated base is placed into a 3 L plastic vessel.

Using a Bamix Gastro 200 Hand held food processor with the beater blade attachment, begin aeration by turning the blender on a at full speed (approx. 17000 rpm) and introducing the blender to the base then lifting the blender out of the base to introduce air into the mixture. This process is then repeated at a rate of approx 200 per minute for 3 minutes. At this stage a 'meringue'-like foam forms.

One kilogram unaerated composition is aerated at any one time.

EXAMPLE 2

Specific Gravity Measurement protocol

A 25 ml cup was taken and filled completely with water. The filled cup was weighed and a mass noted down. The cup was then emptied and the process repeated a further two times to obtain an average.

|  | A (g) | B (g) | C (g) | AVE (g) | Standard dev | % error |
|---|---|---|---|---|---|---|
| Water | 44.55 | 43.17 | 42.68 | 43.466667 | 0.97 | 2 |

It is this average mass that is used to calculate the specific gravity of the test samples.

A 4 Kg batch was prepared to the standard protocol.

EXAMPLE 3

Standard protocol for making a soufflé.

| Trade name | % w/w raw material in formula | |
|---|---|---|
| DI Water | 43.05 | Weigh empty suitable size beaker and blade. Record the weight. Add #1 and begin heating to 70 C. Cover beaker with foil to minimize evaporation. |
| Purac HS88 | 0.42 | Add Purac HS88 and mix for 1 min |
| Lexamine S-13/ Tegoamid S18 | 1.35 | Add Lexamine S-13/Tegoamid S18 and mix until melted |
| Genamin BTLF | 0.70 | Add Genamin BTLF and mix until melted |
| PEG 6000 DS C | 0.02 | Add PEG 6000 DS C and mix until melted |
| Lanette S3/ Hydrenol MY/ Ginol 1618 | 6.00 | Add Lanette S3/Hydrenol MY/Ginol 1618 and mix until melted |
| White Mineral Oil SU 70 | 1.00 | Add White Mineral Oil SU 70 and mix for 30 mins at 70 C. |
| DI Water | 31.31 | Quench water added to cool mixture down to 55-60* C. |
| Wacker Belsil HL 999 | 1.00 | Make a premix of Wacker Belsil HL 999 and DI Water. At 58-56° C. add premix to main batch |
| DI Water | 4.00 | |
| Disodium EDTA | 0.10 | Make a premix of #11 and #12 and heat to 50* C. Once dissolved add this to main batch and mix for 15 mins. |
| DI Water | 2.00 | |
| Luviset Clear | 5.00 | Make a premix of #13 and #14. Add this to main batch |
| DI Water | 2 | |
| Dow Corning ® CF-0410 Cosmetic Fluid | 0.40 | At ~40* C. Add Dow Corning ® CF-0410 Cosmetic Fluid and mix for 10 mins |
| Perfume | 0.2500 | Add perfume at ~30* C. |
| Glydant Plus Liquid | 0.400 | Add Glydant Plus Liquid and Keravis PE once cool |
| Keravis PE | 1.00 | |
|  | 100.00 | Aeration instructions - Using a food hand blender, mix (1 Kg at a time) of room temperature mixture in a continuous 'up and down' motion for 3 minutes until 'meringue' like foam forms |

The Soufflé was split into twenty one viscosity jars (50 g in each) and placed in the 50° C. oven.

Three samples were then removed at different intervals (30 mins, 1 hour, 2 hours, 3 hours, 4 hours and 24 hours). A final 3 were left out as an initial control sample.

Following each removal, the samples were allowed to equilibrate for 3 hours.

Once cooled each sample was opened and very carefully scraped into the 25 ml cup ensuring the cup is fully filled and the rim is flat. The cup was then weighed and its mass noted down. This was then repeated for the other samples and an average taken The specific gravity was measured by dividing the mass of soufflé by the mass of the water in the cup.

| Cooking time | A | B | C | AVE | Standard dev | % error |
|---|---|---|---|---|---|---|
| initial | 20.99 | 20.90 | 20.79 | 20.89 | 0.10 | 0 |
| SG | 0.48 | 0.48 | 0.48 | 0.48 | 0.00 | 0 |
| 30 mins | 19.03 | 19.37 | 19.02 | 19.14 | 0.20 | 1 |
| SG | 0.44 | 0.45 | 0.44 | 0.44 | 0.00 | 1 |
| 1 hour | 18.85 | 18.83 | 19.03 | 18.90 | 0.11 | 1 |
| SG | 0.43 | 0.43 | 0.44 | 0.43 | 0.00 | 1 |
| 2 hours | 19.59 | 19.81 | 19.41 | 19.60 | 0.20 | 1 |
| SG | 0.45 | 0.46 | 0.45 | 0.45 | 0.00 | 1 |
| 3 hours | 19.08 | 20.04 | 20.10 | 19.74 | 0.57 | 3 |
| SG | 0.44 | 0.46 | 0.46 | 0.45 | 0.01 | 3 |
| 4 hours | 21.33 | 22.10 | 21.63 | 21.69 | 0.39 | 2 |
| SG | 0.49 | 0.51 | 0.50 | 0.50 | 0.01 | 2 |
| 24 hours | 25.04 | 25.30 | 25.73 | 25.36 | 0.35 | 1 |
| SG | 0.58 | 0.58 | 0.59 | 0.58 | 0.01 | 1 |

The data shows that heating for from 30 minutes to 3 hours at 50° C. provides a composition with a reduced specific gravity and so enhanced consumer sensory benefit.

EXAMPLE 4

Yield Stress Measurement protocol

Three 1 Kg batches of soufflé were prepared with 0%, 1% and 5% Keravis® added to each.

Each Soufflé was split into four viscosity jars (50 g in each). Three were placed in a 25*C oven (to simulate room temperature) and three in a 50*C oven (to simulate cooking)

These samples were left in the oven overnight (16 hours from 4 pm to 8 am the following day).

The following morning the samples were removed from the oven and were allowed to equilibrate for 3 hours.

Yield Stress of each were recorded using the Brookfield Rheometer using Spindle 72 (secondary point)

| Yield stress | | | | |
|---|---|---|---|---|
| Spindle | | 72-secondary | | |
| Unaerated | | | | |
| Torque | | 47.13 | | |
| Yield stress | | 150.83 | | |
| | A | B | Ave | Stdev |
| 0% ker uncooked | | | | |
| Yield stress | 74.22 | 88.01 | 81.115 | 9.751003 |
| Torque | 23.11 | 27.5 | | |
| 0% ker cooked | | | | |
| Yield stress | 77.72 | 84.31 | 81.015 | 4.659834 |
| Torque | 24.29 | 26.35 | | |
| 1% ker uncooked | | | | |
| Yield stress | 98.65 | 96.41 | 97.53 | 1.583919 |
| Torque | 30.83 | 29.78 | | |
| 1% ker cooked | | | | |
| Yield stress | 131.4 | 130.83 | 131.115 | 0.403051 |
| Torque | 41.06 | 40.89 | | |
| 5% ker uncooked | | | | |
| Yield stress | 109.27 | 108.35 | 108.81 | 0.650538 |
| Torque | 34.15 | 34.07 | | |
| 5% ker cooked | | | | |
| Yield stress | 140.49 | 136.98 | 138.735 | 2.481945 |
| Torque | 43.9 | 42.81 | | |

The data sows that adding hydrolysed vegetable protein improves the yield stress of a heated aerated composition.

The invention claimed is:

1. Foamed personal care composition comprising hydrolysed vegetable protein PG-propyl silanetriol and obtained by aerating a base composition followed by heating at from 30 to 100° C. for from 10 minutes to 100 hours, wherein the foamed personal care composition is in the form of a non-aerosol aqueous conditioner composition that further comprises a lamellar phase in which a cationic surfactant is dispersed, wherein the foamed personal care composition is packaged in an aerated form.

2. Composition according to claim 1 obtained by heating at from 36 to 75° C.

3. Composition according to claim 1 obtained by heating at from 45 to 55° C.

4. Composition according to claim 1 obtained by heating at from 30 to 100° C. for from 10 min to 90 min.

5. Composition according to claim 1 obtained by heating at from 30 to 100° C. for from 20 min to 50 min.

6. Composition according to claim 1 wherein the foamed personal care product contains at least 40% by volume of air.

* * * * *